United States Patent
Moinard et al.

(10) Patent No.: US 11,603,613 B2
(45) Date of Patent: Mar. 14, 2023

(54) REINFORCED NON-WOVEN FABRIC, ASSEMBLY INCLUDING SUCH A FABRIC, AND METHOD FOR TREATING A NON-WOVEN FABRIC

(71) Applicant: APLIX, Le Cellier (FR)

(72) Inventors: Nathalie Moinard, Sainte Luce sur Loire (FR); Thierry Marche, La Chapelle Basse Mer (FR)

(73) Assignee: APLIX, Le Cellier (FR)

(*) Notice: Subject to any disclaimer, the term of this patent is extended or adjusted under 35 U.S.C. 154(b) by 375 days.

(21) Appl. No.: 15/543,469

(22) PCT Filed: Jan. 15, 2016

(86) PCT No.: PCT/FR2016/050082
§ 371 (c)(1),
(2) Date: Jul. 13, 2017

(87) PCT Pub. No.: WO2016/113516
PCT Pub. Date: Jul. 21, 2016

(65) Prior Publication Data
US 2017/0362756 A1   Dec. 21, 2017

(30) Foreign Application Priority Data
Jan. 16, 2015   (FR) ...................... 1550348

(51) Int. Cl.
*D04H 1/70*   (2012.01)
*A61F 13/49*   (2006.01)
(Continued)

(52) U.S. Cl.
CPC ......... *D04H 1/70* (2013.01); *A61F 13/15756* (2013.01); *A61F 13/49015* (2013.01);
(Continued)

(58) Field of Classification Search
CPC ............ D04H 1/70; D04H 1/49; D04H 1/558; D04H 1/58; B32B 3/02; B32B 5/022;
(Continued)

(56) References Cited

U.S. PATENT DOCUMENTS

| | | | |
|---|---|---|---|
| 5,569,528 A | 10/1996 | Van der Loo et al. | |
| 5,620,779 A * | 4/1997 | Levy | D04H 1/559 428/167 |
| 8,148,598 B2 * | 4/2012 | Tsang | A61F 13/15658 604/367 |

FOREIGN PATENT DOCUMENTS

| | | |
|---|---|---|
| EP | 1218170 A1 | 11/2004 |
| EP | 2401147 B1 | 6/2015 |

(Continued)

OTHER PUBLICATIONS

International Search Report and English language translation issued in International App. No. PCT/FR2016/050082 dated May 2, 2016 (8 pages).

(Continued)

*Primary Examiner* — Vincent Tatesure
(74) *Attorney, Agent, or Firm* — Bookoff McAndrews, PLLC

(57) ABSTRACT

A non-woven sheet (10) comprises at least one zone of reinforcement (20a, 20b, 20c, 20d) in which fibers and/or filaments constituting the sheet are bonded together in a reinforcing pattern (22) comprising a plurality of geometric shapes (24), the zone of reinforcement extending over the entire length (L) of the sheet measured in the longitudinal direction (X1), and over a width (l1, l2) strictly less than the width (l) of the sheet (10) measured in a lateral direction (Y1) orthogonal to the longitudinal direction (X1). The sheet (10) thus further comprises at least one non-reinforced zone (30a, 30b). Because of the bonding between the fibers and/or filaments, the elongation of the reinforced zone (20a, 20b,

(Continued)

20c, 20d) under the effect of a given force exerted in a longitudinal direction of the sheet (10) is less than the elongation of the non-reinforced zone under the effect of the same force. Such a sheet (10) may be used in particular for fabricating a laminated assembly.

23 Claims, 8 Drawing Sheets

(51) Int. Cl.
| | |
|---|---|
| *D04H 1/49* | (2012.01) |
| *D04H 1/558* | (2012.01) |
| *B32B 5/02* | (2006.01) |
| *B32B 27/12* | (2006.01) |
| *B32B 5/26* | (2006.01) |
| *B32B 7/12* | (2006.01) |
| *B32B 5/04* | (2006.01) |
| *B32B 5/14* | (2006.01) |
| *D04H 5/08* | (2012.01) |
| *B32B 7/04* | (2019.01) |
| *B32B 3/02* | (2006.01) |
| *D04H 5/00* | (2012.01) |
| *B32B 5/06* | (2006.01) |
| *A61F 13/15* | (2006.01) |
| *D04H 1/58* | (2012.01) |

(52) U.S. Cl.
CPC ............... *B32B 3/02* (2013.01); *B32B 5/022* (2013.01); *B32B 5/04* (2013.01); *B32B 5/06* (2013.01); *B32B 5/142* (2013.01); *B32B 5/26* (2013.01); *B32B 7/04* (2013.01); *B32B 7/12* (2013.01); *B32B 27/12* (2013.01); *D04H 1/49* (2013.01); *D04H 1/558* (2013.01); *D04H 1/58* (2013.01); *D04H 5/00* (2013.01); *D04H 5/08* (2013.01); *B32B 2250/44* (2013.01); *B32B 2307/51* (2013.01)

(58) Field of Classification Search
CPC .. B32B 5/04; B32B 5/06; B32B 5/142; B32B 5/26; B32B 7/04; B32B 7/12; B32B 27/12
USPC ......................................................... 442/350
See application file for complete search history.

(56) References Cited

FOREIGN PATENT DOCUMENTS

| | | |
|---|---|---|
| JP | S52-124983 A | 10/1977 |
| JP | S61-201064 A | 9/1986 |
| JP | 2003-507585 A | 2/2003 |
| JP | 2013-520578 A | 6/2013 |
| RU | 2100498 C1 | 12/1997 |
| RU | 2673772 C1 | 11/2018 |
| WO | 01/00915 A1 | 1/2001 |
| WO | 03/008192 A1 | 1/2003 |

OTHER PUBLICATIONS

Office Action issued in Japanese Patent Application No. 2017-537431, dated Oct. 1, 2019 (8 pages).

* cited by examiner

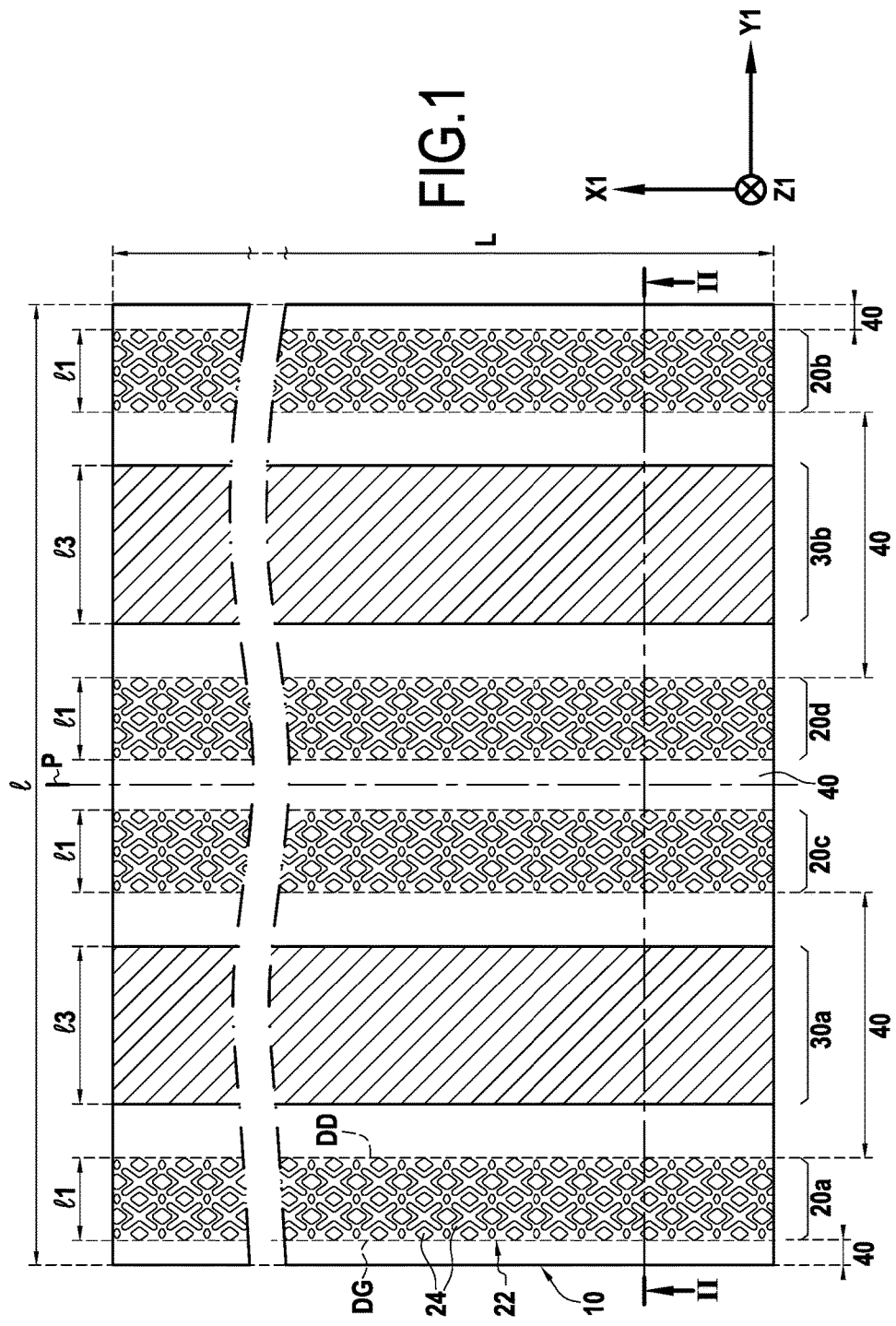

REINFORCED NON-WOVEN FABRIC, ASSEMBLY INCLUDING SUCH A FABRIC, AND METHOD FOR TREATING A NON-WOVEN FABRIC

CROSS-REFERENCE TO RELATED APPLICATIONS

This application is the U.S. national phase entry under 35 U.S.C. § 371 of International Application No. PCT/FR2016/050082, filed on Jan. 15, 2016, which claims priority to French Patent Application No. 1550348, filed on Jan. 16, 2015, the entireties of which are herein incorporated by reference.

FIELD OF THE INVENTION

The present disclosure relates to non-woven sheets and to laminated assemblies including such sheets.

The present disclosure relates more particularly to non-woven sheets and to laminated assemblies suitable for use in the field of hygiene, in particular for fabricating diapers elastic ears.

In the present disclosure, the term "non-woven" covers any non-woven fabric coming within the definition commonly accepted by the person skilled in the art, typically textiles made of fibers and/or filaments that are tangled together and held together in order to form a sheet.

BACKGROUND

On production lines for laminated assemblies, and as shown in FIG. 16, a non-woven sheet is subjected to a tension F in its longitudinal direction (corresponding to the machine direction of the production line, i.e. the direction in which the sheet travels along the line).

Because of this tension F, the sheet is subjected to a reduction in its width. This phenomenon, known as "neckdown" or as "shrinkage", is shown diagrammatically in FIG. 16. In its initial state, without tension, the sheet ($N_i$) presents a width $l_i$ and a length $L_i$. Once the sheet ($N_f$) is subjected to a longitudinal tension F, its length ($L_f$) is increased while its width ($l_f$) is reduced. Its thickness may also be increased. On a production line requiring a non-woven sheet of useful width $l_u$, one solution for mitigating this reduction in sheet width consists in using a sheet of actual width $l_a$ that is greater than $l_u$, with the difference between the useful width $l_u$ and the actual width $l_a$ corresponding to the predicted reduction in the width of the sheet as a result of neckdown. Nevertheless, that solution presents drawbacks: each time there is a change in the speed of the sheet while starting or stopping the production line, the longitudinal tension applied to the sheet changes and the width of the sheet varies correspondingly. In order to ensure that the width of the sheet at the end of the production line lies within a desired tolerance range, it is sometimes necessary to cut off the side edges of the sheet. However, even though the width of the sheet can be adjusted in that way, its mechanical performance—and in particular its elongation capacity in the transverse direction—can vary locally depending on the magnitude of the neckdown phenomenon, also giving rise to local variations in the performance of the laminated assembly that includes said sheet.

In production lines, another solution consists in unwinding non-woven sheets without any tension, e.g. by transporting them on a conveyor belt. In order to form a laminated assembly, those sheets are then assembled without tension to an elastic film. Nevertheless, when the laminated assembly is subsequently unwound, the non-woven sheets making it up are subjected to the neckdown phenomenon, giving rise to deformation in the laminated assembly, thereby preventing it from being guided properly on downstream production lines.

SUMMARY

One of the objects of the present invention is to provide a method of processing a sheet and a sheet as processed in this way, making it possible to remedy the above-mentioned drawbacks of the prior art.

More particularly, one of the objects of the invention is to make it possible to control the width of a non-woven sheet while such a sheet is being unwound under tension on a production line.

This object is achieved with a non-woven sheet extending in a longitudinal direction and a lateral direction orthogonal to the longitudinal direction, said sheet comprising:
  at least one zone of reinforcement in which fibers and/or filaments constituting the sheet are bonded together in a reinforcing pattern comprising a plurality of geometric shapes, the zone of reinforcement extending over the entire length of the sheet measured in the longitudinal direction, and over a width strictly less than the width of the sheet measured in the lateral direction; and
  at least one non-reinforced zone;
  whereby the elongation of the reinforced zone under the effect of a given force exerted in the longitudinal direction is strictly less than the elongation of the non-reinforced zone under the effect of the same force.

The term "bonding" when used of the fibers and/or filaments should be understood herein to mean any bonding that increases their cohesion. More particularly, such bonding may comprise locally increasing the volumetric density of the sheet (particularly but not exclusively locally increasing the density of fibers and/or filaments), obtained by any mechanical bonding (e.g. by compression) and/or thermal bonding and/or chemical bonding of the fibers and/or filaments, or indeed by a combination of several such types of bonding. For example, the bonding may be welding.

Consequently, the stiffness of the sheet is greater in each zone of reinforcement than in the non-reinforced zones.

When the sheet is subjected to longitudinal tension, its elongation in the longitudinal direction is limited compared with a non-reinforced prior art sheet when subjected to the same longitudinal tension, thereby also limiting the deformation that is induced in the lateral direction.

In the present disclosure, the elongation of a zone of the sheet is expressed as a percentage relative to its initial length.

A sheet of the invention may for example be constituted by a non-woven fabric obtained using dry-laid (dry process), wet-laid (wet process), or spun-laid technology (melt spinning/extrusion process), and consolidated by mechanical, thermal, chemical, and/or adhesive bonding.

In an example, the sheet is constituted by a consolidated carded type non-woven sheet, in particular a non-woven sheet of the Spunlace type, i.e. it is consolidated by hydro-entanglement.

The reinforcing pattern is generally constituted by repeating a unit pattern in the longitudinal direction of the sheet.

In an example, the geometric shapes constituting the reinforcing pattern are discrete elements, which may for example be circles, crosses, lozenges, oblong shapes, etc.

The term "discrete" is used of elements that are discontinuous or indeed isolated, so as to be distinct from one another. These elements may thus be defined by a closed outline.

The term "plurality of geometric shapes" is used to mean at least two discrete elements of respective outlines of the at least two discrete elements that may be identical, similar, or different.

Some shapes may be solid. Others may be constituted by a closed-loop curve that presents, over its entire extent, an inner margin and an outer margin.

In an example, the geometric shapes of the reinforcing pattern in each zone of reinforcement are arranged in such a manner that any straight line extending in the lateral direction of the sheet intersects at least one of said shapes. The reinforcement of the sheet is thus continuous over its entire length. Localized manifestations of the neckdown phenomenon are thus avoided.

In another example, the geometric shapes of the reinforcing pattern of each zone of reinforcement are arranged in such a manner that any straight line that is inclined relative to the lateral direction by an angle lying strictly in the range 0 to 90°, more particularly strictly in the range 0 to 45°, still more particularly inclined at an angle of about 24°, intersects at least one of said shapes of said zone.

The zone of reinforcement is generally defined by a left limit straight line DG and a right limit straight line DD, said parallel limit lines extending in the longitudinal direction of the sheet. The weld pattern is contained entirely between these two lines and each line is tangential to at least one shape of the reinforcing pattern.

In an example, the bonding percentage in the zone of reinforcement is greater than 10%, or more precisely greater than 15%, or indeed greater than 25%.

In an example, the bonding percentage in the zone of reinforcement is less than 90%, or more particularly less than 70%.

In the present disclosure, the bonding percentage in the zone of reinforcement is equal to the percentage of the area of said segment covered by the geometric shapes of the reinforcing pattern. It is generally measured on a segment of the zone of reinforcement having a width equal to the width of said zone and a length equal to an integer number of reinforcing unit patterns.

By way of example, this integer number may be selected so that the length of the segment is greater than the width of the reinforcing zone.

First and second adjacent zones of reinforcement are generally separated by an intermediate strip without reinforcement, extending in the longitudinal direction, and preferably presenting a width that is equal to at least 10% of the smaller of the widths of the two reinforcing zones.

In an example, the width of each zone of reinforcement represents at most 80% of the width of the sheet, preferably at most 60% of the width of the sheet.

For each reinforcing zone, it is possible to define a useful portion that is defined by a left limit margin BG and by a right limit margin BD.

The limit margin on one side of the useful portion is defined as follows:

It includes the "end" points of the reinforcing pattern, in other words the points that are furthest towards the outside on said side (in the lateral direction), with this applying for each coordinate along an axis extending in the longitudinal direction of the sheet.

Where appropriate, the limit margin also includes straight line segments extending in the lateral direction and interconnecting its portions constituted by the above-defined end points.

Each limit margin may thus be a straight line, a curved line, or a combination of one or more straight and/or curved line segments.

It is possible to measure the bonding percentage over the useful portion of the zone of reinforcement along a segment of said useful portion extending over a length that is equal to the length of the unit pattern. It is equal to the percentage of the surface area of said segment that is covered by the geometric shapes of the reinforcing pattern.

The bonding percentage over the useful portion of the zone of reinforcement may for example be greater than 15%, or more precisely greater than 20%, or indeed greater than 35%.

Generally, the bonding percentage over the useful portion of the zone of reinforcement is less than 90%, more particularly less than 75%.

In an example, the elongation of the reinforced zone under the effect of a traction force of 5 Newtons (N) exerted in the longitudinal direction is less than the elongation of the non-reinforced zone under the effect of the same force.

The elongation of the zone of reinforcement under the effect of said given force exerted in the longitudinal direction may for example be at least 5% less than, and more particularly at least 15% less than, or indeed more particularly at least 50% less than the elongation of the non-reinforced zone under the effect of the same force. For example, if the non-reinforced zone presents an elongation of 17% when subjected to a traction force of 5 Newtons, then the elongation of the zone of reinforcement is less than or equal to 12%.

In an example, the sheet further comprises at least one activated zone extending over a width that is less than the width of the sheet, and in which the non-woven fabric is activated.

A non-woven sheet generally presents little capacity for elongation compared with the capacity for elongation of an elastic film. When such a sheet is to be laminated on an elastic film in order to form a laminated assembly, it is sometimes necessary to apply prior processing locally or to its entire surface for the purpose of reducing the cohesion of its structure, so that once it has bonded to the elastic film the resulting laminated assembly can be stretched easily (with a lesser force, e.g. 10 N).

Activation consists in subjecting the non-woven fabric to stretching. It acts locally and in non-reversible manner to increase the capacity of the non-woven fabric to lengthen. Typically, activation is performed in the lateral direction of the sheet.

The activated non-woven fabric, in cross-section view, generally presents a wavy shape in its activated zone so long as it is not subjected to any external tension.

The present disclosure also provides a laminated assembly comprising at least one first sheet as defined above together with at least one elastic film connected to said first sheet.

In an example, the laminated assembly comprises at least a second non-woven sheet, the at least one elastic film being interposed between the first and second sheets.

In an example, the first sheet comprises at least one first zone of reinforcement, and the second sheet is a sheet of the above-defined type, having at least one second zone of reinforcement.

By way of example, the first and second zones of reinforcement may overlap over at least one overlap zone of predetermined width.

In an example, the projections of the respective reinforcing patterns of the first and second zones of reinforcement coincide over at least one zone of the laminated assembly.

Consideration is given herein to the projections of the reinforcing patterns onto a plane orthogonal to the thickness of the laminated assembly (in other words a plane orthogonal to the stacking direction of the layers of the laminated assembly).

In another example, the reinforcing pattern of the first zone of reinforcement and the reinforcing pattern of the second zone of reinforcement are different.

In another example, the projection of the respective reinforcing patterns of the first and second zones of reinforcement in the Z direction are arranged in such a manner that any straight line extending in the lateral direction of the sheet intersects the projections of the geometric shapes of the reinforcing patterns of the first and second zones of reinforcement. In particular, the projection of the respective reinforcing patterns of the first and second zones of reinforcement in the Z direction are arranged in such a manner that any straight line inclined relative to the lateral direction at an angle lying strictly between 0 and 90°, more particularly lying strictly between 0 and 45°, still more particularly inclined at an angle of about 24°, intersects the projection of the geometric shapes of the reinforcing patterns of the first and second zones of reinforcement.

Each zone of reinforcement of each sheet may be offset in the lateral direction relative to an elastic portion of the laminated assembly.

The term "elastic portion" of the laminated assembly is used to mean a portion of the laminated assembly including the elastic film and adapted to be stretched under the effect of a stretching force exerted in the lateral direction and adapted to return substantially to its initial shapes and dimensions after said stretching force has been released. By way of example, it may be a portion that conserves residual deformation or remanence after elongation and release (also known as "permanent set" or "SET" for short) of less than 20%, more particularly less than 15%, in certain circumstances less than 5% of its initial dimension (before elongation) for an elongation of 100% of its initial dimension, at ambient temperature (23° C.).

In another example, at least one first zone of reinforcement of the first sheet and at least one second zone of reinforcement of the second sheet overlap over at least one overlap zone of predetermined width, and one of the first zone of reinforcement of the first sheet and the second zone of reinforcement of the second sheet extends beyond said overlap zone towards an elastic portion of the laminated assembly in its lateral direction.

The present disclosure also provides a method of processing a non-woven sheet, said sheet extending in a longitudinal direction and in a lateral direction orthogonal to the longitudinal direction, the method comprising at least one reinforcing step during which, over at least one zone of reinforcement of the sheet extending over the entire length of the sheet as measured in the longitudinal direction and over a width that is strictly less than the width of the sheet as measured in its lateral direction, fibers and/or filaments constituting the sheet are bonded together using a reinforcing pattern comprising a plurality of geometric shapes in such a manner that the elongation of the reinforced zone under the effect of a given force exerted in the longitudinal direction is less than the elongation of a non-reinforced zone of the sheet under the effect of the same force.

During the reinforcing step, the cohesion of the fibers and/or filaments of the sheet is increased. More particularly, the volumetric density of the sheet is increased locally (particularly but not exclusively the density of fibers and/or filaments is increased locally), by mechanical bonding (e.g. by compressing the sheet), and/or thermal bonding (by heating the sheet), and/or chemical bonding of the fibers and/or filaments, or indeed by a combination of a plurality of such types of bonding. By way of example, the fibers and/or filaments may be locally welded.

By way of example, the reinforcement step may be performed by hot calendering.

In variants, it may also be performed by laser, by ultrasound, by embossing (cold calendering), or indeed by a combination of at least two such technologies.

In an example, the method further comprises an activation step in which the non-woven fabric is stretched in order to activate it over at least one activated zone of the sheet.

In an example, the method further comprises, prior to the reinforcement step, a step of adjusting the width of the sheet.

Several embodiments are described in the present disclosure. Nevertheless, unless specified to the contrary, characteristics described with reference to any one embodiment may be applied to any other embodiment.

BRIEF DESCRIPTION OF THE DRAWINGS

The invention can be well understood and its advantages appear better on reading the following detailed description of several embodiments shown as non-limiting examples. The description refers to the accompanying drawings, in which:

FIG. 1 shows a non-woven sheet according to an embodiment of the present invention, seen from above;

FIG. 2 is a cross-section of the FIG. 1 non-woven sheet, on plane II-II of FIG. 1;

DETAILED DESCRIPTION

Figure 3:
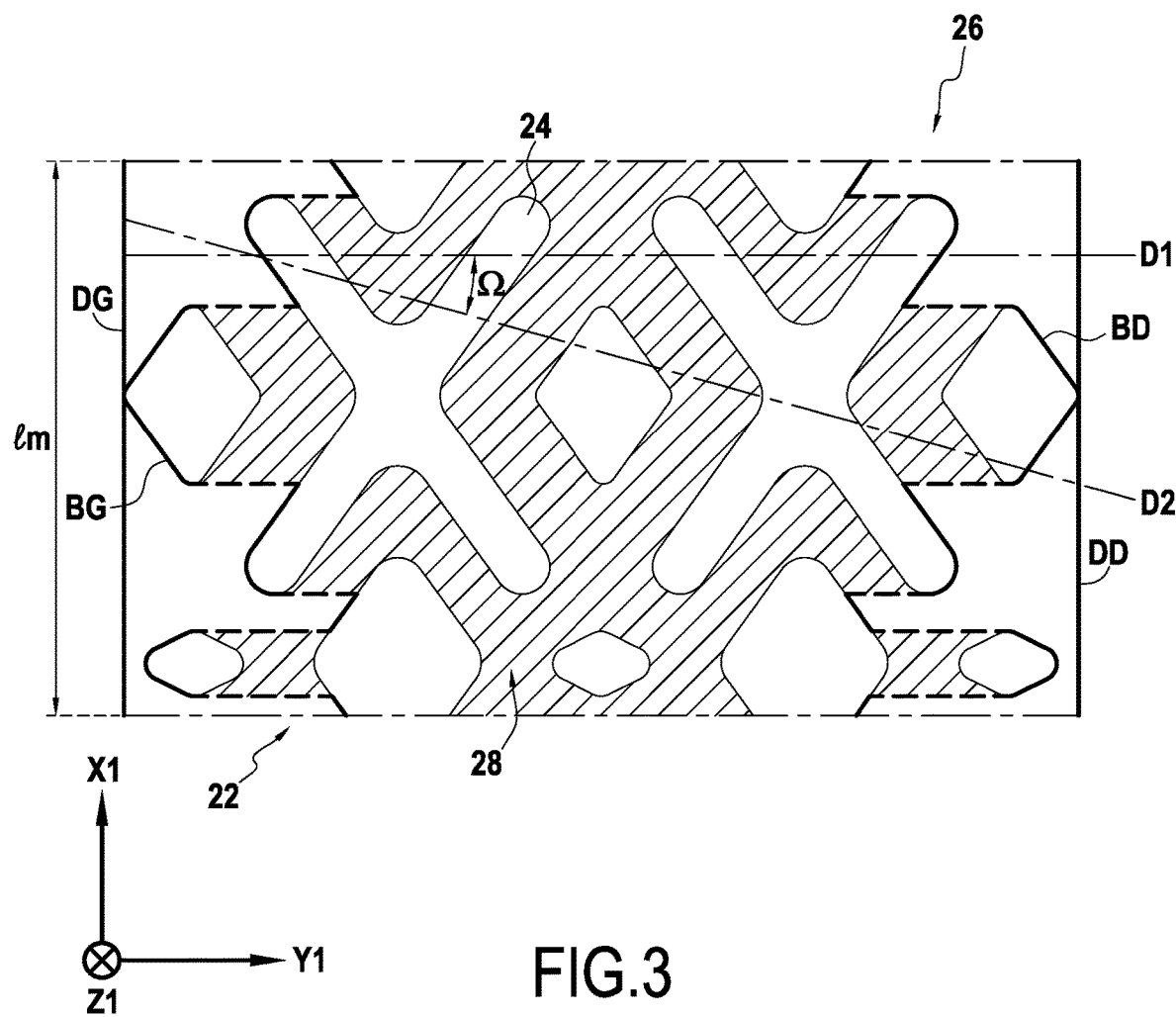
FIG. 3 shows the useful portion of the reinforcing zone on a segment of said zone corresponding to a unit pattern.

FIGS. 1 and 2 show a non-woven sheet 10 according to a first embodiment of the present invention.

The sheet 10 is defined relative to a longitudinal direction X1 in which its length L is measured, and a lateral direction Y1 that is orthogonal to X1, in which its width l is measured. These two longer dimensions of the sheet are shown in plan view of FIG. 1.

By way of example, the sheet 10 is made as a Spunlace type non-woven fabric, constituted by a plurality of fibers consolidated by hydro-entanglement, and commonly used in the field of hygiene for its softness and its natural capacity for deformation.

Because of its high capacity for deformation, Spunlace non-woven fabric is particularly subject to the above-described neckdown phenomenon. When tension is applied thereto in a given direction, it undergoes considerable deformation in the orthogonal direction. Consequently, on a production line where it is subjected to considerable longitudinal tension, a Spunlace non-woven sheet shrinks significantly in its width direction.

In accordance with the invention, the sheet 10 is locally reinforced in order to avoid the neckdown phenomenon.

As shown in FIG. 1, it thus includes zones of reinforcement 20a, 20b, 20c, and 20d where the fibers constituting the sheet are bonded together with a reinforcing pattern 22 comprising a plurality of geometric shapes 24, each zone of reinforcement 20a, 20b, 20c, and 20d extending over the entire length L of the sheet 10 and over a width that is strictly less than the width l of the sheet 10.

The reinforced zones 20a, 20b, 20c, and 20d are bordered by non-reinforced zones 40.

Because of the bonding provided locally between the fibers, the sheet 10 is stiffened in the zones of reinforcement 20a, 20b, 20c, and 20d. Because of this stiffening, the lengthening of a reinforced zone of the sheet under the effect of a given force exerted in the longitudinal direction X1 is less than the lengthening of a non-reinforced zone, for the same force.

Consequently, when the sheet is subjected to longitudinal tension, its deformation induced in the lateral direction is limited compared with a non-reinforced sheet.

In order to measure the elongation of one zone of reinforcement or of one non-reinforced zone, it is possible by way of example to use the following methods:

The non-woven sheet is prepared in a normal atmosphere, as defined by the standard ASTDM 5170, at a temperature 23° C.±2° C. and at relative humidity of 50%±5%.

The equipment used is a dynamometer complying with the standard EN 10002, in particular a Synergie 200H, available from the supplier NTS Systems Corp. USA, together with utilization software TESTWORKS 4.04 B.

A cutter or scissors is/are used for preparing a sample having a width of 10 millimeters (mm) in the cross direction (CD) of the sheet and a length of 150 mm in the machine direction (MD) of the sheet, in a zone of reinforcement or in a non-reinforced zone.

The sample is placed between the jaws of the dynamometer.

The following parameters are selected:
distance between jaws: 100 mm;
machine speed: 500 millimeters per minute (mm/min);
number of cycles: 1; and
pre-load: 0.1 N.

The sample is stretched in its width direction (corresponding to the longitudinal direction of the sheet) until it breaks, by moving the jaws vertically.

A curve is then obtained by plotting stretching force as a function of percentage elongation. It is thus possible to define the percentage elongation at 5 N, which corresponds to the elongation to which the sheet is subjected when being unwound on the production line.

The value of 5 N is not limiting, and in other measurement methods it might be different, e.g. equal to 10 N.

FIG. 1 shows four distinct zones of reinforcement of the sheet 10: two lateral zones of reinforcement 20a and 20b located in the lateral margins of the sheet and of width l1, and two central zones of reinforcement 20c and 20d of width l1 and separated from each other by a non-reinforced zone 40.

The sheet thus presents a plane of symmetry P parallel to its longitudinal direction X1.

The number, the width, and the locations of the zones of reinforcement of a sheet of the invention may nevertheless vary as a function of needs and of the subsequent use intended for the sheet. Thus, a sheet may have a single zone of reinforcement or a number of zones of reinforcement that is other than four. Furthermore, although such symmetrical configurations provide advantages, in particular of enabling two identical elastic lugs to be fabricated simultaneously from a laminate using such a sheet by cutting along the plane of symmetry P, the zone(s) of reinforcement of a sheet are not necessarily in the side margins of the sheet nor are they necessarily centered relative to the sheet. Furthermore, they need not necessarily be arranged symmetrically. The widths of the zones of reinforcement in a given sheet may also be adjusted depending on circumstances.

Nevertheless, and as shown in FIG. 1, two adjacent zones of reinforcement are preferably spaced apart by a non-reinforced zone 40 extending in the longitudinal direction and presenting a width of not less than 10% of the smaller width from among the widths of two zones of reinforcement.

In the example shown, the non-woven sheet 10 also has an activated zone 30a, 30b in each non-reinforced zone 40 situated between two adjacent zones of reinforcement 20a, 20b, 20c, where an activated zone 30a, 30b is in the form of a continuous strip of width l3 in which the fibers of the non-woven fabric have been activated.

Preferably, the width l3 of an activated zone is greater than the width l1 of the zone of reinforcement. More particularly, the width l3 of an activated zone is 1.5 times greater than the width l1 of the zone of reinforcement.

For reasons of concision, only one zone of reinforcement 20a of the sheet 10 is described in detail below. All of the elements described with reference to that zone of reinforcement 20a are nevertheless applicable to the other zones of reinforcement 20b, 20c of the sheet 10.

As shown in FIG. 1, the zone of reinforcement 20a is in the form of a strip defined between a left limit straight line DG and a right limit straight line DD, said parallel limit lines extending in the longitudinal direction X1. The reinforcing pattern 22 is contained entirely between these two lines DG and DD, and each line is tangential to at least one shape 24 of the reinforcing pattern 22.

Preferably, the width l1 of the zone of reinforcement 20a (in other words the distance measured in the lateral direction Y1 between the lines DG and DD) represents no more than 80% of the width l of the sheet 10, preferably no more than 60% of the width l of the sheet 10.

In the example, in register with the reinforcing pattern 22, the fibers of the sheet 10 are compressed and welded together, possibly involving as much as complete melting of the material from which they are made, the fibers as such disappearing and being replaced by a zone of film, thereby locally increasing the density of the sheet. By way of example, such reinforcement may be obtained by hot calendering, as described in greater detail below.

The thickness e1 of the sheet 10 in the zone of reinforcement 20a is less than the thickness e of the sheet in the non-reinforced zones 40, as can be seen in FIG. 2.

The reinforcing pattern 22 contained in the zone 20a is typically constituted by regularly repeating a unit pattern 26 of length lm in the longitudinal direction X1.

The reinforcing unit pattern 26 of the zone 20a is shown in greater detail in FIG. 3.

In this example, it is made up of a combination of discrete solid geometric shapes, specifically crosses and lozenges.

The bonding percentage in the zone of reinforcement 20a, in other words the bonding percentage over a segment of the zone of reinforcement corresponding to the unit pattern 26, is preferably greater than 10% and less than 90%, or more precisely lies in the range 25% to 70%.

A useful portion 28 of the zone of reinforcement 20a is also defined, being defined by a left limit margin BG and a right limit margin BD. In the example of FIG. 1, the limit margins BG and BD extend generally in the longitudinal direction X1.

The left and right limit margins BG and BD of the useful portion 28 are shown in FIG. 3.

The left margin BG includes the end points of the reinforcing pattern 22 that are the furthest to the left (in the lateral direction Y1), and this applies for each coordinate taken along an axis extending in the longitudinal direction X1. These end points are represented by a continuous bold line in FIG. 3. The margin also comprises straight line segments (represented in discontinuous bold lines, to the left in FIG. 3) extending in the lateral direction Y1 and connecting together the portions of the margin that are constituted by the left end points as defined above.

The right margin BD comprises the end points of the reinforcing pattern 22 that are the furthest to the right (in the lateral direction Y1), with this applying to each coordinate taken along an axis extending in the longitudinal direction X1. These end points are represented by a continuous bold line on the right in FIG. 3. The margin also comprises straight line segments (represented by discontinuous bold lines to the right in FIG. 3) extending in the lateral direction Y1 and connecting together the portions of margin that are constituted by the above-defined right end points.

The bonding percentage over a useful portion 28 of the zone of reinforcement 20a, as measured over a segment having a length Lm (the unit pattern in this example) is preferably greater than 15%, and more particularly greater than 20% and less than 90%.

As is well known to the person skilled in the art, the fibers and/or filaments of a non-woven fabric are held together as a result of consolidation performed over the entire extent of tangled fibers and/or filaments during fabrication of the non-woven fabric, which consolidation may be thermal (calendering, ultrasound, etc.), mechanical (hydro-entanglement, needling, etc.), chemical, or adhesive.

Consolidation provides a certain amount of cohesion for the fibers and/or filaments, enabling them to be manipulated and transported, and in particular to be wound in the form of a roll and to be unwound. Under certain circumstances, consolidation may be performed at a plurality of points that are distributed in substantially uniform manner over the entire width of the non-woven sheet. For example, calendered carded non-woven fabric typically presents thermal consolidation points.

The consolidation points form a pattern that is different from the reinforcing pattern. For simplification purposes, these consolidation points of the non-woven fabric are not shown in the figures.

It should be understood that the consolidation points are clearly to be distinguished from the above-described reinforcing pattern. Consolidation serves to give the sheet a certain amount of initial cohesion over its entire area in order to form a non-woven fabric, whereas the reinforcement provided by the present invention serves to increase locally the initial cohesion that results from that consolidation. The consolidation points of the non-woven fabric are therefore not taken into account when calculating the above-mentioned bonding percentage of the reinforcement.

In an example, the geometric shapes 24 of the reinforcing pattern 22 are arranged in such a manner that any line extending in the lateral direction Y1 of the sheet 10, such as the line D1 in FIG. 3, intersects at least one of said patterns 24. The sheet 10 is thus reinforced continuously over its entire length. Localized manifestations of the neckdown phenomenon are thus avoided.

Still more preferably, the geometric shapes 24 of the reinforcing pattern 22 are arranged in such a manner that any line that slopes relative to the lateral direction Y1 at an angle Ω lying strictly between 0 to 90°, such as the line D2 in FIG. 3, intersects at least one of said shapes 24. In particular, the angle Ω may lie strictly between 0 and 45°.

The above-described reinforcing pattern 22 is nevertheless not limiting, and it is possible for the geometric patterns 24 and the way they are arranged to vary.

In particular, the geometric shapes 24 constituting the reinforcing pattern 22 need not be solid. Thus, in a variant, each shape 24 may be constituted by a closed-loop curve that presents over its entire extent an inside margin and an outside margin.

Figure 4A:
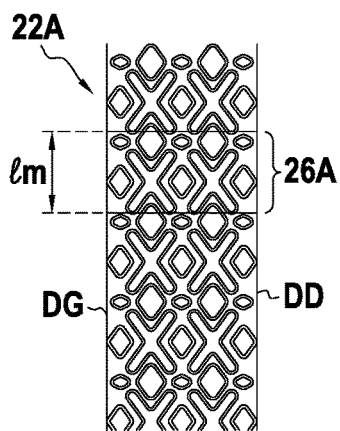
FIGS. 4A, 4B, and 4C show three other examples of reinforcing patterns.

This applies to the reinforcing pattern 22A shown in FIG. 4A: each cross or lozenge 24A in this figure is constituted by a curve forming a closed outline.

Selecting this type of pattern serves to limit the energy needed for creating it, while conserving satisfactory performance. Furthermore, the surface remains soft to the touch.

Figure 4B:
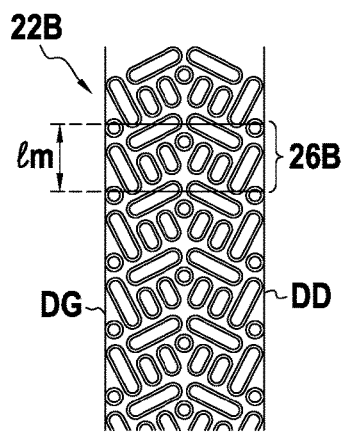
Figure 4C:
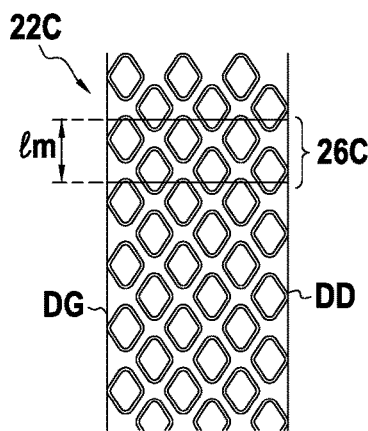

FIGS. 4B and 4C show two other examples of patterns 22B and 22C comprising respectively a combination of circles and oblong shapes (FIG. 4B), and a succession of identical lozenges (FIG. 4C).

In another example, the reinforcing pattern 22 may also have limit margins BG and BD extending in directions that are substantially inclined relative to the longitudinal direction X1, e.g. deviating from that direction in alternation to the left and then to the right, so as to form a zigzag or a sinewave. Such an arrangement can be obtained using calendering rollers pivoting from left to right or from right to left while making a unit reinforcing pattern.

A reinforcing sheet 10 of the above-described type can be used in the fabrication of laminated assemblies, and in particular trilaminates comprising two non-woven sheets and at least one elastic film interposed between said sheets.

Figure 5:
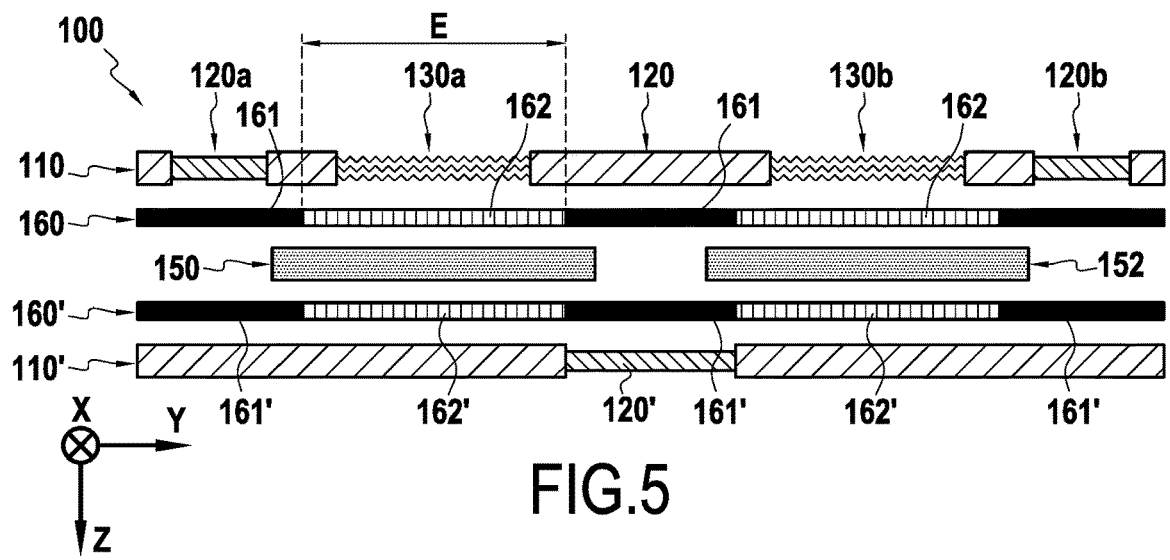
FIG. 5 is a cross-section of a laminated assembly according to an embodiment of the present invention.

A first embodiment of such a laminated assembly 100 is shown in FIG. 5. In obvious manner, the longitudinal and lateral directions X and Y of a laminated assembly need to be considered below as being parallel respectively to the longitudinal and lateral directions of the sheets making up the laminated assembly. The thickness direction Z of the laminated assembly is defined as the stacking direction for the various layers making up the assembly.

The laminated assembly 100 is formed by superposing, in the direction Z:
- a first reinforced non-woven sheet 110 having two zones of reinforcement 120*a* and 120*b* arranged along the lateral margins of the sheet 110, together with two activated zones 130*a* and 130*b* arranged between said zones of reinforcement 120*a* and 120*b*;
- two elastic films 150 and 152 arranged substantially in register with the first and second activated zones 130*a* and 130*b* of the first sheet 110; and
- a second reinforced non-woven sheet 110' having a single zone of reinforcement 120' centered on said sheet 110'.

The non-woven sheets 110, 110' of the laminated assembly and the elastic films 150, 152 interposed between said sheets are connected together by adhesive 160, 160'.

The activated zones 130*a* and 130*b* of the first sheet 110 give it a certain capacity for elongation, locally.

The second sheet, made of a non-woven fabric that is more elastic than the fabric constituting the first sheet 110, is not activated.

Nevertheless, in a variant embodiment, both sheets could be made of non-woven fabric of the same kind.

In the example, the adhesive 160, 160' is applied in solid strips 161 and 161' between the elastic films and on their lateral margins, whereby the elastic films are securely fastened to the sheets 110 and 110', in straight lines or beads 162 and 162' in register with the activated zones 130*a* and 130*b* of the first sheet 110. In a variant, the elastic film may have adhesive applied over its entire width in continuous manner, possibly selecting a thickness for the adhesive that is smaller in certain zones (in particular in the center).

In the example shown, the elastic films 150 and 152 may be stretched between the beads of adhesive 162 and 162', thereby providing the laminated assembly 100 with elasticity.

The zones E situated in register with the central zones of the elastic films 150 and 152 covered in the beads of adhesive 162 and 162' thus constitute portions of the laminated assembly 100 that are said to be "elastic".

In another embodiment, it is possible to envisage that the elastic film is applied directly on the non-woven sheets, thereby obtaining a laminate that does not have any adhesive (or fastener agent), e.g. by applying the sheets onto the elastic film at the outlet from an extruder.

By way of example, and as shown in FIG. 5, each zone of reinforcement 120*a*, 120*b*, 120' of each sheet 110, 110' is offset in the lateral direction Y relative to its elastic portion E.

In the example of FIG. 5, it should also be observed that the zones of reinforcement 120*a*, 120*b* of the first sheet 110 are offset relative to the zone of reinforcement 120' of the second sheet 110', in the lateral direction Y.

In other embodiments, a first zone of reinforcement of the first sheet and a second zone of reinforcement of the second sheet may overlap, in other words they may be positioned in register with each other in the Z direction.

Under such circumstances, the reinforcing pattern in the two superposed zones may be identical or different.

Furthermore, the two zones of reinforcement may optionally have the same width, and the two zones may overlap over their entire width or over a portion only of their width.

Figure 8C:
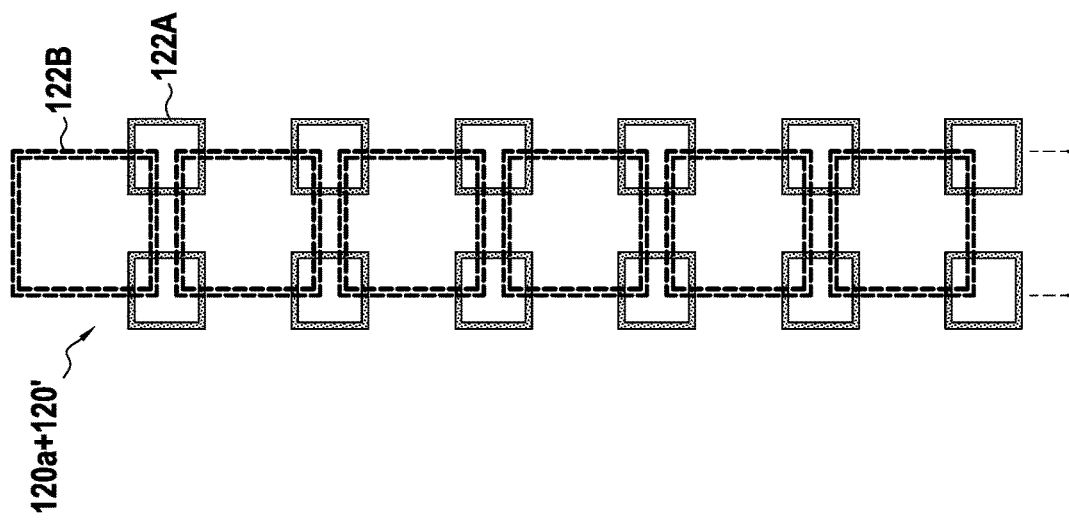
FIG. 8C is a diagram showing the first and second zones of reinforcement of FIGS. 8A and 8B superposed in a plane orthogonal to the thickness direction of the laminated assembly.
Figure 8B:
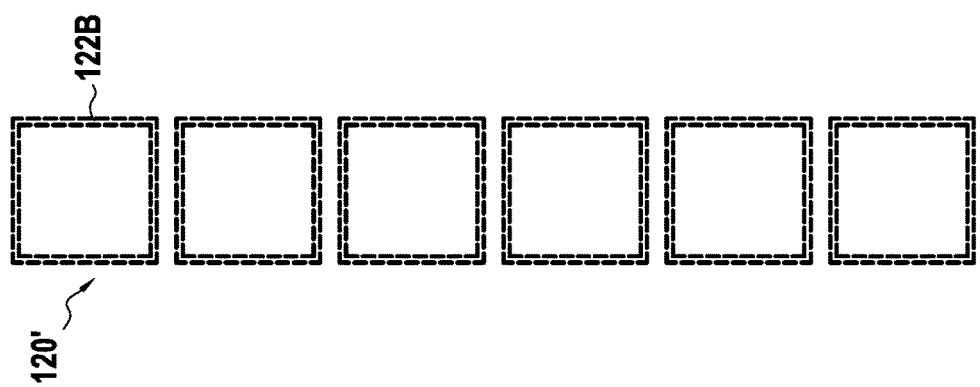
FIGS. 8A and 8B show respectively the first zone of reinforcement of the first non-woven sheet in a variant of the laminated assembly of FIG. 5 and the second zone of reinforcement of the second non-woven sheet in the same laminated assembly.
Figure 8A:
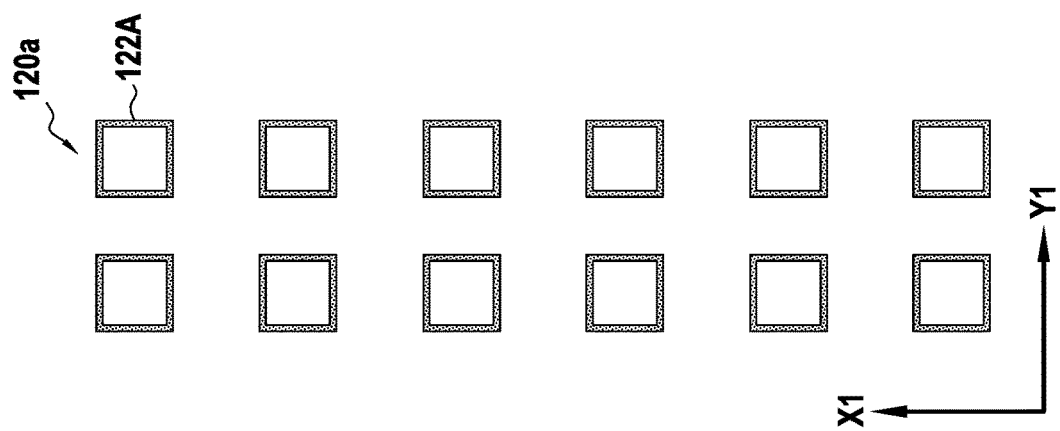

Thus, by way of example, FIG. 8A shows a reinforcing pattern 122A of the first zone of reinforcement 120*a* of the first sheet 110 and FIG. 8B shows a reinforcing pattern 122B of the second zone of reinforcement 120' of the second sheet 110', the two zones of reinforcement 120*a* and 120' presenting different geometric patterns 122A and 122B.

In this embodiment, the first and second zones of reinforcement 120*a* and 120' extend over the entire length of the sheet measured in the longitudinal direction and over a width that is strictly less than the width of the sheet measured in the lateral direction.

FIG. 8C shows the first and second zones of reinforcement 120*a* and 120' that do not present the same width and that overlap over the entire width of the zone of reinforcement 120' and over a portion only of the width of the zone of reinforcement 120*a*. The first and second zones of reinforcement 120*a* and 120' overlap in the central overlap zone ZC.

In this example, it can be seen that the projection in the Z direction of the respective reinforcing patterns 122A and 122B of the first and second zones of reinforcement 120*a* and 120' are arranged in such a manner that any straight line extending in the lateral direction Y1 of the sheet intersects the projection of the geometric shapes of the reinforcing patterns of the first and second zones of reinforcement. In particular, the projection of the respective reinforcing patterns 122A and 122B of the first and second zones of reinforcement 120*a* and 120' in the Z direction are arranged in such a manner that any line that is inclined relative to the lateral direction at an angle lying strictly between 0 and 90°, and still more particularly lying strictly between 0 and 45°, and more particularly inclined at an angle of about 24°, intersects the projection of the geometric shapes of the reinforcing patterns of the first and second zones of reinforcement.

In a particular arrangement, the zones of reinforcement may have reinforcing patterns that are identical or partially identical, and the projections of the respective reinforcing patterns of the first and second zones of reinforcement in the stacking direction may coincide over at least a predetermined width of the laminated assembly.

Figure 6:
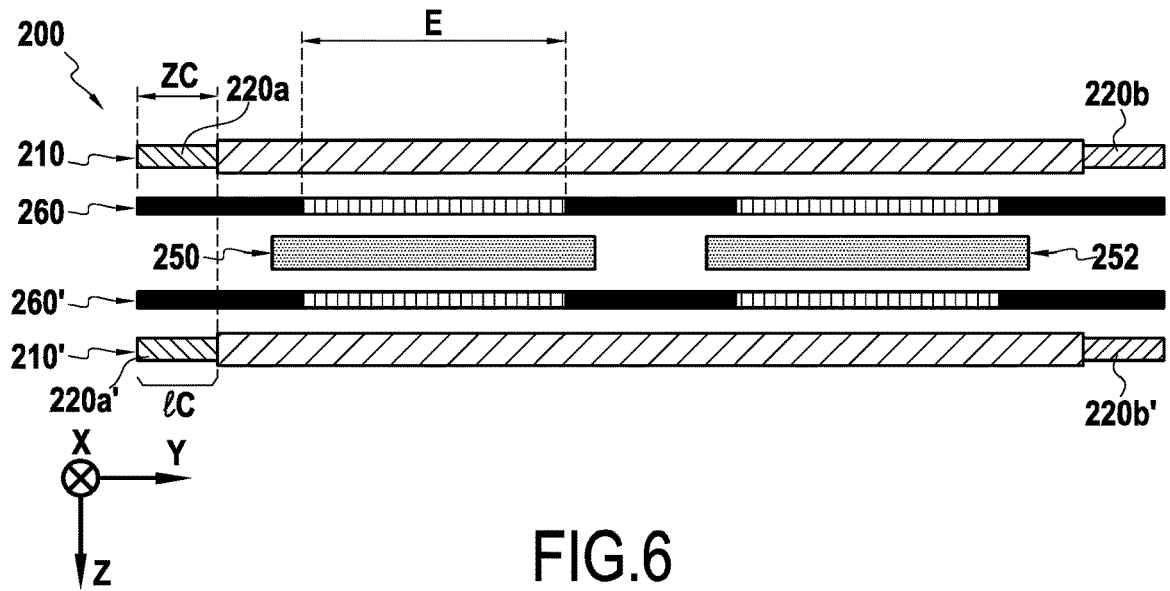
FIG. 6 is a cross-section of a laminated assembly according to another embodiment of the present invention.

FIG. 6 shows a laminated assembly 200 in another embodiment of the invention, and comprising:
- a first reinforced non-woven sheet 210 having two zones of reinforcement 220*a* and 220*b* arranged along lateral margins of the sheet 210;
- a second reinforced non-woven sheet 210' having two zones of reinforcement 220*b* and 220*b* arranged along lateral margins of the sheet 210';
- two elastic films 250 and 252 interposed between the two sheets 210 and 210'; and
- adhesive 260 and 260' connecting together the two elastic films 250, 252 and the non-woven sheets 210, 210'.

The general structure of the laminated assembly, in particular concerning the arrangement of lines and strips of adhesive, is substantially identical to that of FIG. 5 and is therefore not described again.

In this example, a first zone of reinforcement 220*a* forming part of the first sheet overlaps a second zone of reinforcement 220*a*' forming part of the second sheet 210' over an overlap zone referenced ZC in FIG. 6.

The opposite side of the laminated assembly is arranged symmetrically, so it is not described in greater detail below.

In the particular example shown, the zones of reinforcement 220*a* and 220*a*' have the same width and they overlap over this entire width referenced lc (width of the overlap zone).

In a particular provision, the reinforcing patterns of the first and second zones of reinforcement are identical.

Figure 9B:
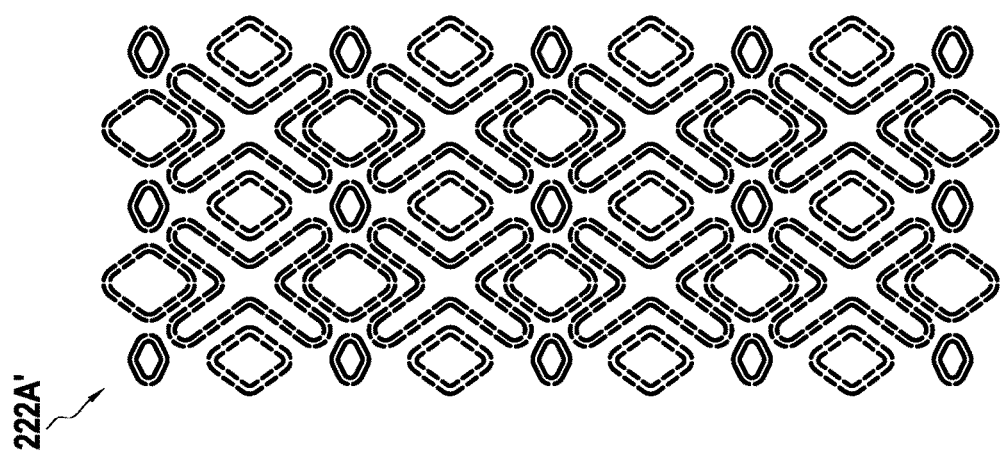
FIGS. 9A and 9B show respectively the first zone of reinforcement of the first non-woven sheet of the laminated assembly of FIG. 6 and the identical, second zone of reinforcement of the second non-woven sheet of the same laminated assembly.
Figure 9A:
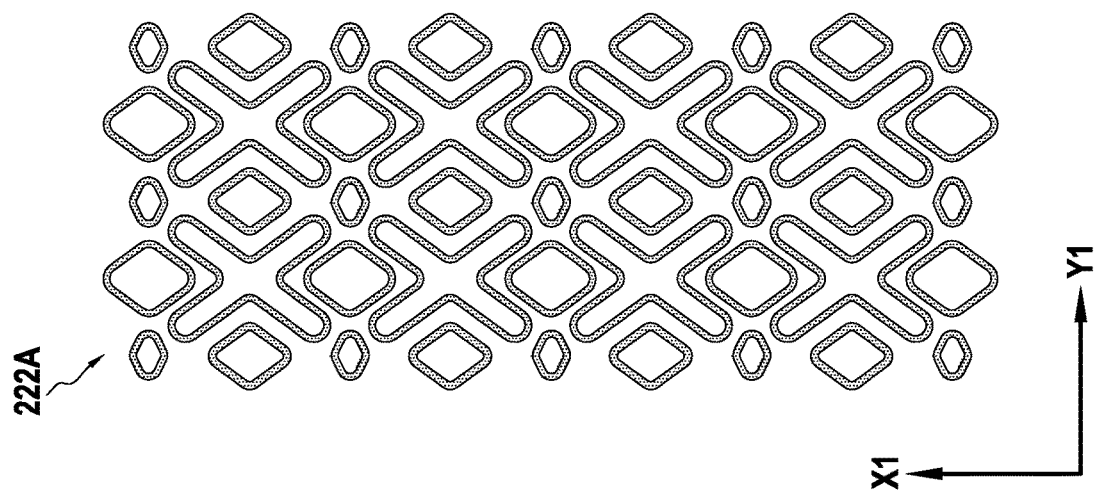

Thus, by way of example, FIG. 9A shows the reinforcing pattern 222A of the first zone of reinforcement 220*a* of the first sheet 210, and FIG. 9B shows the reinforcing pattern 222A' of the second zone of reinforcement 220*a*' of the second sheet 210'.

Figure 10:
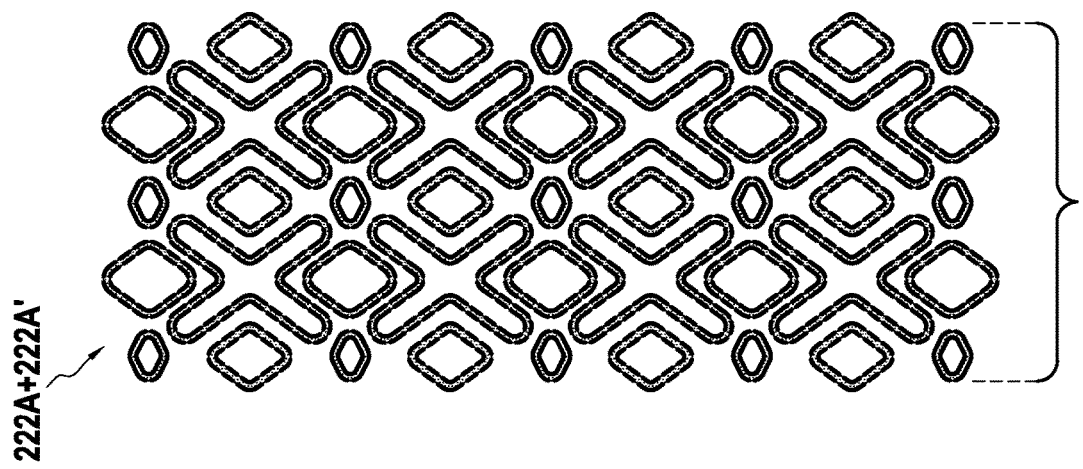
FIG. 10 is a diagram showing the first and second zones of reinforcement of FIGS. 9A and 9B superposed in a plane orthogonal to the thickness direction of the laminated assembly.

In an example, the projections onto a plane orthogonal to the Z direction of the thickness of the laminated assembly 200, the reinforcing patterns 222A, 222A' of the first and second zones of reinforcement 220*a*, 220*a*', coincide over the overlap zone ZC, as shown in FIG. 10.

Figure 11:
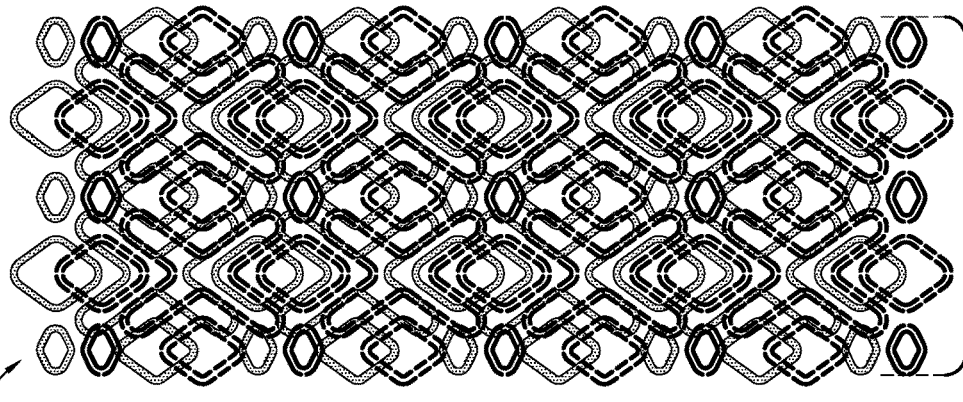
FIG. 11 is a diagram showing the first and second zones of reinforcement of FIGS. 9A and 9B superposed in a second example.

In another example shown in FIG. 11, the respective reinforcing patterns 222A, 222A' of the first and second zones of reinforcement 220*a* and 220*a*' may also be offset in the longitudinal direction X of the laminated assembly, such that their projections no longer coincide.

Figure 12:
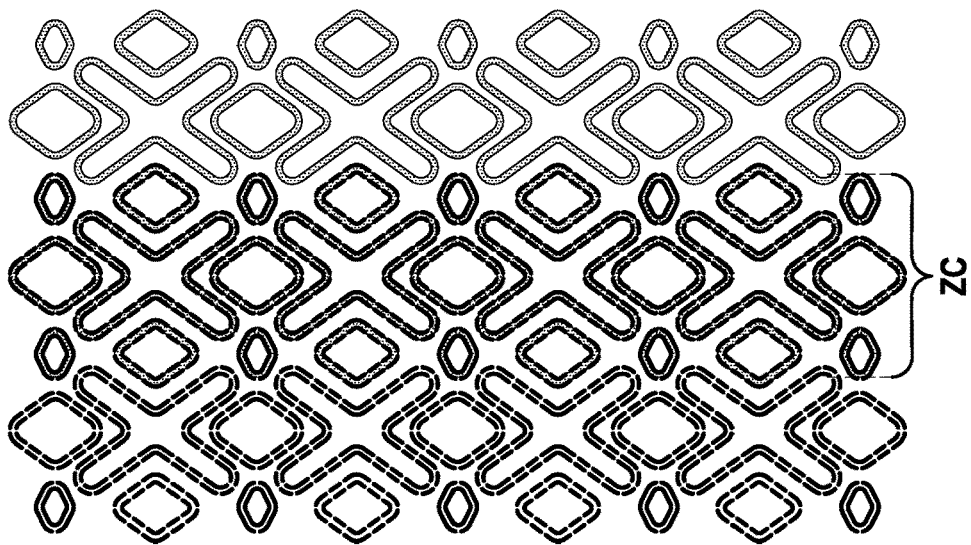
FIG. 12 is a diagram showing the first and second zones of reinforcement of FIGS. 9A and 9B superposed in a third example.

In yet another example, shown in FIG. 12, the two zones of reinforcement 220*a*, 220*a*' may be offset laterally relative to each other, so that the projections of their reinforcing patterns 222A, 222A' continue to coincide over an overlap zone ZC of width lc less than the width of their common pattern.

Figure 13:
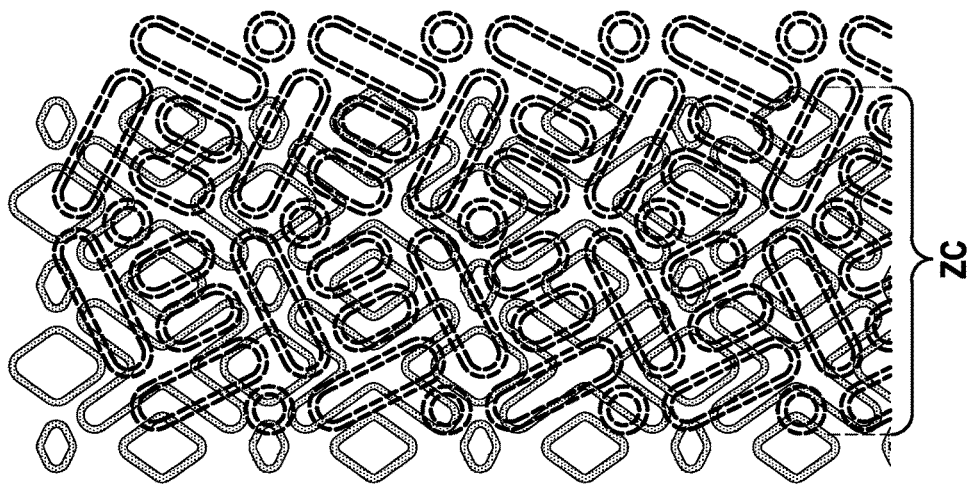
FIG. 13 shows a first zone of reinforcement of a first non-woven sheet and a second zone of reinforcement of a second non-woven sheet superposed in a laminated assembly according to another embodiment of the invention.

FIG. 13 shows two zones of reinforcement presenting different patterns 222A, 222B that are offset relative to each other so as to overlap in a central overlap zone ZC.

Figure 7:
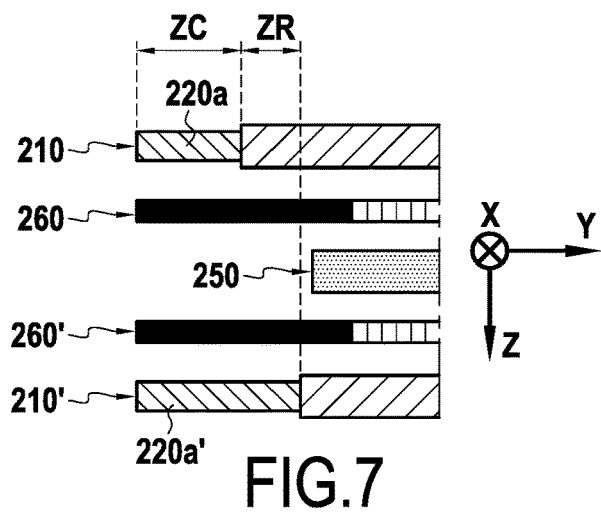
FIG. 7 is a partial cross-section of a laminated assembly in a variant of FIG. 6.

FIG. 7 shows a variant of the FIG. 6 embodiment presenting a particular arrangement of the zones of reinforcement of the non-woven sheets.

As shown in FIG. 7, the second zone of reinforcement 220*a*' of the second non-woven sheet 210' extends beyond the overall zone ZC in the lateral direction Y1 towards an elastic portion E of the laminated assembly.

In the example, the portion of the second zone of reinforcement 220*a*' projecting beyond the overlap zone is referenced ZR. This portion faces a non-reinforced zone of the first sheet 210. It is arranged in the lateral direction Y1 between the overlap zone ZC and the elastic film 250.

It has been found that such provisions make it possible to limit the concentrations of stresses in the laminated assembly, and to increase its ability to withstand rupture.

It should be observed that the example of FIG. 7 does not exclude a zone of reinforcement also projecting beyond the overlap zone ZC beside said zone opposite from the elastic film 250 in the lateral direction Y1.

Furthermore, the zone of reinforcement that extends beyond the overlap zone ZC towards the elastic portion E of the laminated assembly could equally well be the first zone of reinforcement 220*a* of the first sheet 210.

Figure 14:
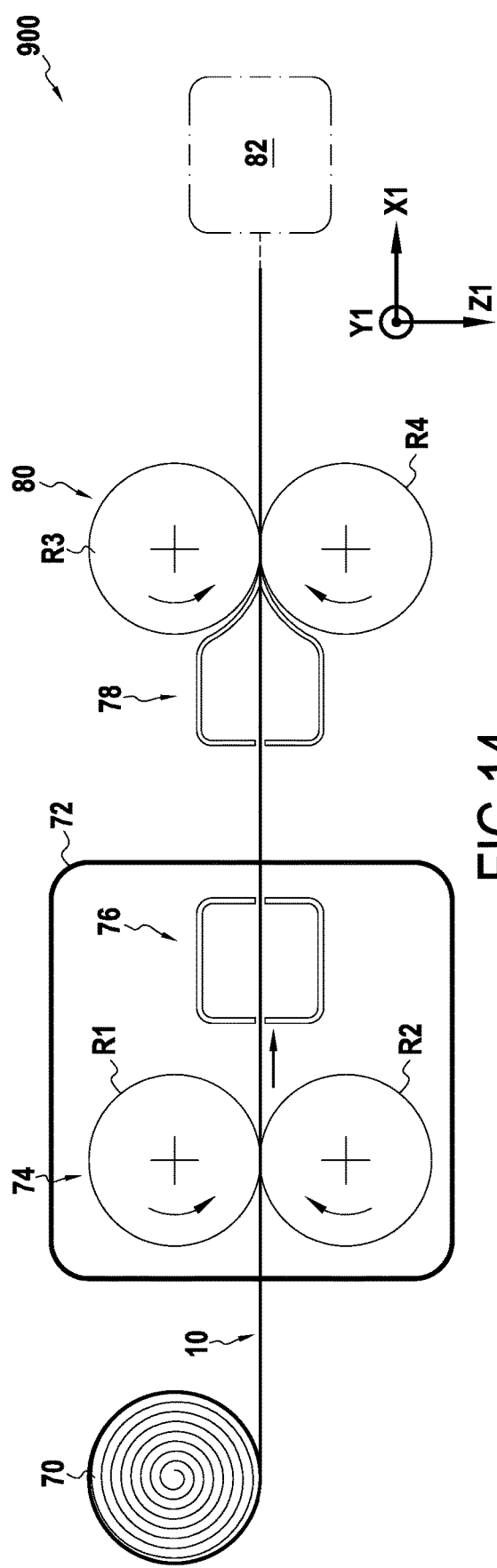
FIG. 14 is a diagram of an installation for processing a non-woven sheet, seen in side view.
Figure 15:
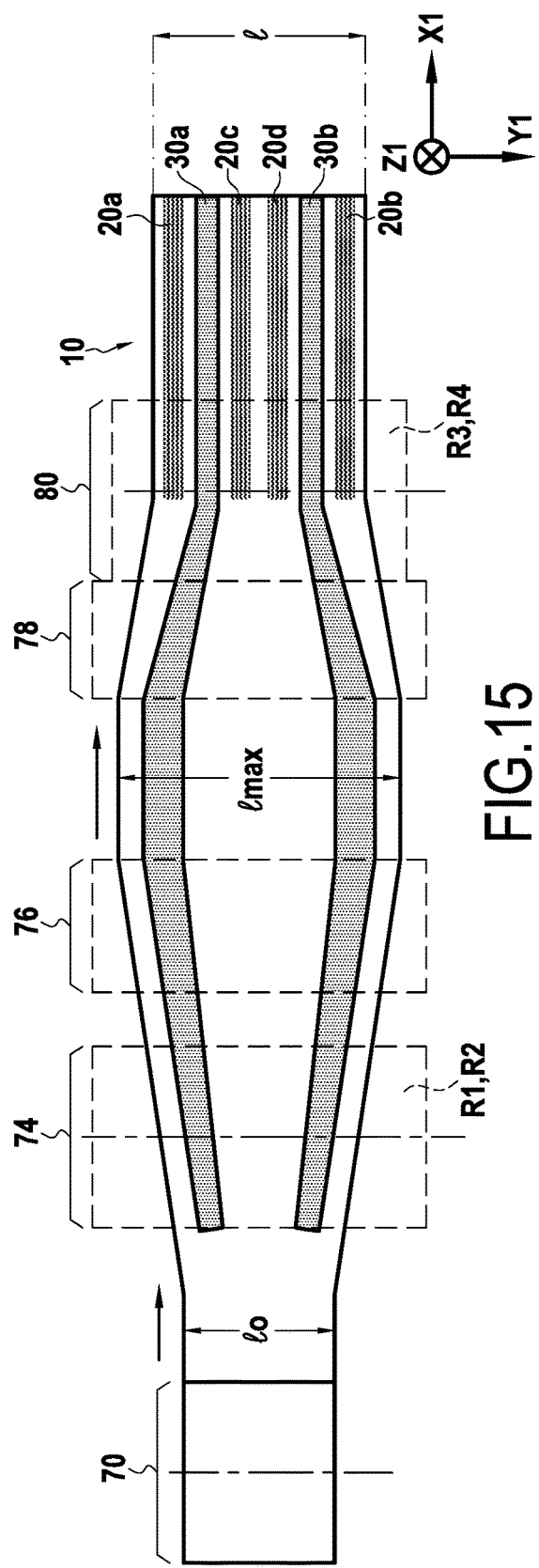
FIG. 15 is a plan view of the non-woven sheet in motion at an instant t in the FIG. 14 processing installation.
Figure 16:
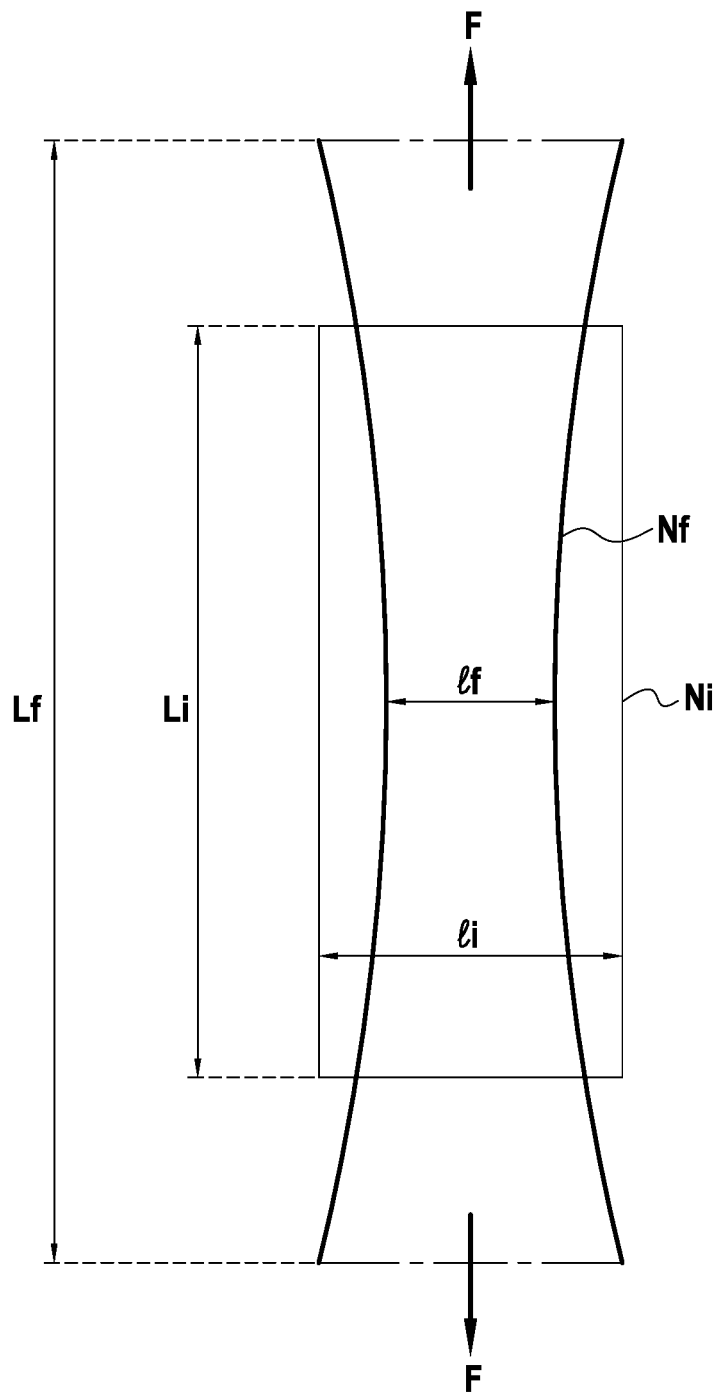
FIG. 16, described above, is a diagram showing the principle of the neckdown phenomenon.

FIG. 14 shows an installation for processing a non-woven sheet 900 and suitable in particular for making a reinforced sheet 10 of the type described with reference to FIGS. 1 and 2 upstream from a production line for producing a laminated assembly.

From upstream to downstream in the travel direction of the sheet for processing (from left to right in the figure) the installation 900 comprises:
  a station 70 for unwinding the non-woven sheet, which is initially prepared in the form of a roll;
  a module 72 for enlarging the sheet, comprising:
    an activation module 74 for activating localized zones of the sheet so as to form the so-called "activated" zones 30*a* and 30*b* of the sheet 10; and
    a stretcher module 76 for stretching the sheet 10 in its lateral direction;
  a width management module 78 for managing the width of the sheet; and
  a reinforcement module 80 for reinforcing the sheet.

In an example, the method of processing the sheet comprises the following steps:

Once it has been unwound, the sheet 10 is activated locally by the activation module 74. In the example, this module 74 has two activation rollers R1 and R2 each having a stack of parallel disks. Since the disks of each roller mesh with the disks of the adjacent roller, the zones of the sheet 10 passing between the disks of the rollers R1 and R2 are stretched in the lateral direction Y1, thereby forming the activated zones 30*a* and 30*b*. In these locations, the fibers of the sheet 10 are broken.

The sheet 10 is then deformed more generally by the stretcher module 76 which generally comprises a plurality of rollers (not shown) having the purpose of stretching the sheet locally. The sheet is stretched therein until it reaches a width lmax greater than the useful width l desired for the laminated assembly that is fabricated downstream in the production line 82.

In the width management module 78, which comprises means for measuring the width of the sheet and means for adjusting this width to a desired value, e.g. by stretching, the width of the sheet 10 is adjusted to the useful width l that it is to conserve throughout the production line 82.

It is then reinforced, immediately downstream from the width management module 78 in order to avoid any variation in its width.

By way of example, the reinforcement is performed by hot calendering.

Under such circumstances, the reinforcement module 80 comprises two heated calendering rollers R3 and R4 that form reinforcing rollers, with at least one of them including rings on its outside surface (four rings in this example) carrying portions in relief reproducing a unit reinforcing pattern. When the sheet 10 passes between the reinforcing rollers, in its longitudinal direction, portions in relief press against the fibers that deform and become welded together under the effect of heat, thereby forming the zones of reinforcement 20*a*, 20*b*, 20*c*, 20*d*.

In variant embodiments and by way of example, the reinforcement could be made by: laser; ultrasound; embossing; or indeed a combination of two or more of these technologies.

The invention claimed is:

1. A non-woven sheet extending in a longitudinal direction and a lateral direction orthogonal to the longitudinal direction, said sheet comprising:
  a first zone of reinforcement in which fibers and/or filaments constituting the sheet are bonded together, in an adhesive-free manner, in a reinforcing pattern comprising a plurality of geometric shapes, the first zone of reinforcement extending over the entire length of the sheet measured in the longitudinal direction, and over a first width strictly less than the width of the sheet measured in the lateral direction, wherein the reinforcing pattern of the first zone of reinforcement is formed on exactly one sheet having an exposed top surface and an exposed bottom surface included in the first zone of reinforcement, the geometric shapes of the reinforcing pattern in the first zone of reinforcement being arranged in such a manner that any straight line extending in the lateral direction of the sheet intersects at least one of said shapes; and a first non-reinforced zone, wherein a first lateral side of the first non-reinforced zone is laterally adjacent to the first zone of reinforcement, the first non-reinforced zone having a second width measured in the lateral direction that is larger than the first width;

the elongation of the first reinforced zone under the effect of a given force exerted in the longitudinal direction being less than the elongation of the first non-reinforced zone under the effect of the same force.

2. A sheet according to claim 1, wherein the geometric shapes of the reinforcing pattern are discrete elements.

3. A sheet according to claim 1, wherein the bonding percentage in the first zone of reinforcement is greater than 10%.

4. A sheet according to claim 1, wherein the bonding percentage in a useful portion of the first zone of reinforcement is greater than 15%.

5. A sheet according to claim 1, wherein the bonding percentage in a useful portion of the first zone of reinforcement is less than 90%.

6. A sheet according to claim 1, wherein the width of the first zone of reinforcement represents at most 80% of the width of the sheet.

7. A sheet according to claim 1, wherein the elongation at 5 N of the first zone of reinforcement is less than the elongation at 5 N of the non-reinforced zone.

8. A sheet according to claim 1, consisting in a consolidated carded type non-woven sheet.

9. A laminated assembly comprising at least a first sheet according to claim 1, and at least one elastic film connected to said first sheet.

10. A laminated assembly according to claim 9, comprising at least a second non-woven sheet, the at least one elastic film being interposed between the first and second sheets.

11. A laminated assembly according to claim 10, wherein the second sheet is a sheet having at least one second zone of reinforcement.

12. A laminated assembly according to claim 11, wherein the first and second zones of reinforcement overlap over at least one overlap zone of predetermined width.

13. A laminated assembly according to claim 12, wherein the projections of the respective reinforcing patterns of the first and second zones of reinforcement coincide over at least one zone of the laminated assembly.

14. A laminated assembly according to claim 12, wherein the projection of the respective reinforcing patterns of the first and second zones of reinforcement in the Z direction are arranged in such a manner that any straight line extending in the lateral direction of the sheet intersects the projections of the geometric shapes of the reinforcing patterns of the first and second zones of reinforcement.

15. A laminated assembly according to claim 9, wherein each zone of reinforcement of each sheet is offset in the lateral direction relative to an elastic portion of the laminated assembly.

16. A laminated assembly according to claim 15, wherein at least one first zone of reinforcement of the first sheet and at least one second zone of reinforcement of the second sheet overlap over at least one overlap zone of predetermined width, and one of the first zone of reinforcement of the first sheet and the second zone of reinforcement of the second sheet extends beyond said overlap zone towards an elastic portion of the laminated assembly in its lateral direction.

17. A method of processing a non-woven sheet, said sheet extending in a longitudinal direction and in a lateral direction orthogonal to the longitudinal direction, the method comprising at least one reinforcing step during which, over at least one zone of reinforcement of the sheet extending over the entire length of the sheet as measured in the longitudinal direction and over a width that is strictly less than the width of the sheet as measured in its lateral direction, fibers and/or filaments constituting the sheet are bonded together using a reinforcing pattern comprising a plurality of geometric shapes in such a manner that the elongation of the reinforced zone under the effect of a given force exerted in the longitudinal direction is less than the elongation of a non-reinforced zone of the sheet under the effect of the same force, wherein the processing method forms the non-woven sheet according to claim 1.

18. A processing method according to claim 17, wherein the reinforcement step is performed by hot calendering.

19. A processing method according to claim 17, further comprising an activation step during which the non-woven fabric is stretched in order to activate it over at least one zone of the sheet.

20. A processing method according to claim 17, further comprising, prior to the reinforcement step, a step of adjusting the width of the sheet.

21. The non-woven sheet of claim 1, further including a second zone of reinforcement in which fibers and/or filaments constituting the sheet are bonded together, in an adhesive-free manner, in a reinforcing pattern comprising a plurality of geometric shapes, the second zone of reinforcement extending over the entire length of the sheet measured in the longitudinal direction, and over a third width strictly less than the width of the sheet measured in the lateral direction, wherein a second lateral side of the first non-reinforced zone is laterally adjacent to the second zone of reinforcement.

22. The non-woven sheet of claim 21, further including a second non-reinforced zone, wherein a first lateral side of the second non-reinforced zone is laterally adjacent to the second zone of reinforcement, the second non-reinforced zone having a fourth width measured in the lateral direction that is less than the second width.

23. The non-woven sheet of claim 22, further including a third zone of reinforcement in which fibers and/or filaments constituting the sheet are bonded together, in an adhesive-free manner, in a reinforcing pattern comprising a plurality of geometric shapes, the third zone of reinforcement extending over the entire length of the sheet measured in the longitudinal direction, and over a fifth width strictly less than the width of the sheet measured in the lateral direction, wherein a second lateral side of the second non-reinforced zone is laterally adjacent to the third zone of reinforcement.

* * * * *